(12) United States Patent
Yamashita et al.

(10) Patent No.: US 11,591,426 B2
(45) Date of Patent: Feb. 28, 2023

(54) COPOLYMER, WETTING AGENT, MEDICAL DEVICE, AND METHOD FOR PRODUCING SAME

(71) Applicant: Toray Industries, Inc., Tokyo (JP)

(72) Inventors: Kyohei Yamashita, Otsu (JP); Takeshi Ishigaki, Otsu (JP); Masataka Nakamura, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 284 days.

(21) Appl. No.: 17/035,860

(22) Filed: Sep. 29, 2020

(65) Prior Publication Data
US 2021/0015960 A1    Jan. 21, 2021

Related U.S. Application Data

(62) Division of application No. 16/085,860, filed as application No. PCT/JP2017/010824 on Mar. 17, 2017, now abandoned.

(30) Foreign Application Priority Data

Mar. 31, 2016   (JP) ................ 2016-071298

(51) Int. Cl.
| | | |
|---|---|---|
| A61L 27/34 | (2006.01) | |
| A61L 29/00 | (2006.01) | |
| C08F 220/36 | (2006.01) | |
| C08F 220/54 | (2006.01) | |
| C08F 220/56 | (2006.01) | |
| C09D 133/24 | (2006.01) | |
| G02B 1/00 | (2006.01) | |
| C08F 220/00 | (2006.01) | |
| G02C 7/04 | (2006.01) | |
| G02B 1/04 | (2006.01) | |
| A61L 29/08 | (2006.01) | |
| A61L 12/14 | (2006.01) | |
| C08F 220/28 | (2006.01) | |

(52) U.S. Cl.
CPC ............ *C08F 220/36* (2013.01); *A61L 12/14* (2013.01); *A61L 27/34* (2013.01); *A61L 29/085* (2013.01); *C08F 220/54* (2013.01); *C08F 220/56* (2013.01); *C09D 133/24* (2013.01); *G02B 1/043* (2013.01); *G02C 7/04* (2013.01); *A61L 2400/10* (2013.01); *A61L 2430/16* (2013.01); *C08F 220/283* (2020.02)

(58) Field of Classification Search
CPC .... C08F 220/36; C08F 220/54; C08F 220/56; C08F 220/283; A61L 27/34; A61L 29/085; A61L 2400/10; A61L 2430/16; C09D 133/24; G02B 1/043; C02C 7/04
See application file for complete search history.

(56) References Cited

U.S. PATENT DOCUMENTS

| | | |
|---|---|---|
| 4,054,722 A | 10/1977 | Yoshida et al. |
| 4,458,001 A | 7/1984 | Taylor |
| 4,582,868 A | 4/1986 | Ogawa et al. |
| 4,948,480 A | 8/1990 | Christy et al. |
| 5,124,421 A | 6/1992 | Ulbrich et al. |
| 6,521,715 B1 | 2/2003 | Ma |
| 9,395,559 B2 | 7/2016 | McCabe et al. |
| 2003/0068433 A1* | 4/2003 | McGee |
| 2009/0173045 A1 | 7/2009 | Lai et al. |
| 2010/0056647 A1 | 3/2010 | Graham et al. |
| 2010/0166985 A1 | 7/2010 | Brockmeyer et al. |
| 2015/0111043 A1 | 4/2015 | Takimoto et al. |

FOREIGN PATENT DOCUMENTS

| | | |
|---|---|---|
| CN | 103788289 A | 5/2014 |
| CN | 103788290 A | 5/2014 |
| CN | 103788292 A | 5/2014 |
| EP | 0306246 A2 | 3/1989 |
| JP | 4885678 A | 11/1973 |
| JP | 522431 A | 1/1977 |
| JP | 59130853 A | 7/1984 |
| JP | 59171848 A | 9/1984 |
| JP | 01111094 A | 4/1989 |
| JP | 0222555 A | 1/1990 |
| JP | 1072427 A | 3/1998 |
| JP | 2002143668 A | 5/2002 |
| JP | 2004045626 A | 2/2004 |
| JP | 2008532060 A | 8/2008 |
| JP | 2011512546 A | 4/2011 |
| JP | 2012501311 A | 1/2012 |
| JP | 2014114430 A | 6/2014 |

* cited by examiner

OTHER PUBLICATIONS

International Search Report and Written Opinion for International Application No. PCT/JP2017/010824, dated Jun. 13, 2017, 8 pages.

*Primary Examiner* — Alma Pipic
(74) *Attorney, Agent, or Firm* — RatnerPrestia

(57) ABSTRACT

Disclosed are: a polymer for treating the surface of a medical device such as a contact lens to suppress the reduction in lubricity of the device even when the device is scrubbed; a medical device having the polymer on the surface so that the reduction in lubricity over time is suppressed; and a wetting agent containing the polymer. The polymer for treating the surface is a copolymer which is water-soluble and includes as constitutional units the following monomers A and B: monomer A: a monomer containing a (meth)acryloyl group and an ester or amide structure in a molecule, in which the ester or amide structure is not constituted by including a part of the (meth)acryloyl group; monomer B: a monomer containing a (meth)acrylamide group in a molecule and having a structure different from that of the monomer A.

10 Claims, 1 Drawing Sheet

COPOLYMER, WETTING AGENT, MEDICAL DEVICE, AND METHOD FOR PRODUCING SAME

CROSS REFERENCE TO RELATED APPLICATIONS

This application is a divisional of U.S. patent application Ser. No. 16/085,860, filed Sep. 17, 2018, which is a U.S. National Phase application of PCT/JP2017/010824, filed Mar. 17, 2017, which claims priority to Japanese Patent Application No. 2016-071298, filed Mar. 31, 2016, the entire disclosures of each of these applications being incorporated herein by reference in their entireties for all purposes.

FIELD OF THE INVENTION

The present invention relates to a copolymer, a medical device having the copolymer on the surface, and a wetting agent comprising the copolymer. The wetting agent comprising the copolymer is suitable as an external wetting agent for ophthalmic lenses, particularly contact lenses.

BACKGROUND OF THE INVENTION

A medical device that comes into direct contact with a part of a human body is required to have biocompatibility on its surface. In order to achieve biocompatibility, it is considered important to control the adhesion of substances such as water, protein, and lipid.

One of the problems with ophthalmic lenses, in particular contact lenses, among medical devices, is initial discomfort for the wearer immediately after wearing the lens, caused by an increased frictional force between the lens surface and the cornea or eyelid. It is thought that the increased frictional force can result in increased risk of corneal damage as well as deterioration of wearing comfort.

For example, high water content soft contact lenses, which are made of hydrous gels (hydrogels) formed through polymerization of hydrophilic monomers such as 2-hydroxyethyl methacrylate (HEMA) in the presence of a small amount of a crosslinking agent, have a problem in that, while having enhanced water wettability due to copolymerized acidic components such as acrylic acid, they have poor lubricity on their lens surfaces.

On the other hand, because low or no water content soft contact lenses often employ hydrophobic monomers, thus having poor lubricity and even poor water wettability, they are considered to require surface modification treatments to impart hydrophilicity.

Improving the lubricity of a lens surface leads to reduction in initial discomfort immediately after wearing the lens, so that a way to impart lubricity to lens surfaces by various polymers has been devised.

Patent Document 1 discloses a method of imparting lubricity to the surface of a high water content lens, the method comprising: adding a hydrophilic polymer polyvinylpyrrolidone (PVP) to a packaging solution included in a blister pack; immersing a contact lens in the solution; and carrying out steam sterilization.

Patent Document 2 discloses a method of imparting lubricity to the surface of a silicone hydrogel lens, the method comprising: immersing a contact lens in a packaging solution containing acid-terminated PVP produced by a reaction between hydroxylated poly(vinylpyrrolidone) or poly(vinylpyrrolidone-co-allyl alcohol) and succinic anhydride; and carrying out steam sterilization.

Patent Document 3 describes in the example a compound obtained by copolymerizing the following six components: n-butyl acrylate, styrol, amide acrylate, acrylic acid ester of N-β-hydroxyethyl pyrrolidone and sodium salt of mono-β-methoxyethyl maleate. However, since the compound is used in an aqueous dispersion, it is suspended in a liquid and not soluble in water. In addition, the document does not describe the use of the above compound for medical use.

PATENT DOCUMENTS

Patent Document 1: JP 2008-532060 A
Patent Document 2: JP 2011-512546 A
Patent Document 3: JP 48-85678 A

SUMMARY OF THE INVENTION

According to the invention of Patent Document 1, PVP has a problem in that although PVP can be applied to disposable contact lenses, PVP cannot be applied to lenses for continuous use, because of the fact that, despite the ability of PVP to maintain lubricity over a long period of time, the lubricity is reduced by scrubbing with a cleaning solution for soft contact lenses.

According to the invention of Patent Document 2, although there is no specific description about the lubricity of the contact lens to be obtained, there may be a possibility that sufficient lubricity to withstand scrubbing cannot be obtained. In addition, although an acid-terminated PVP was specifically prepared in the Example by a method involving, as described above, reacting hydroxylated poly(vinylpyrrolidone) and poly(vinylpyrrolidone-co-allyl alcohol), which are polymers, with succinic anhydride, the method has a problem in that it is difficult to control the number of the acid end introduced.

An object of the present invention is to provide, by a different approach from the above-mentioned prior art, a polymer for treating the surface of a medical device such as a contact lens to suppress the reduction in lubricity of the device even when the device is scrubbed; a medical device having the polymer on its surface so that the reduction in lubricity over time is suppressed; and a wetting agent comprising the polymer.

In order to achieve the above object, the present invention has the following constitution:

1. A copolymer which is water-soluble and comprises as constitutional units the following monomers A and B:
   monomer A: a monomer containing a (meth)acryloyl group and an ester or amide structure in a molecule, wherein the ester or amide structure is not constituted by including a part of the (meth)acryloyl group;
   monomer B: a monomer containing a (meth)acrylamide group in a molecule and having a structure different from that of the monomer A.

2. A medical device comprising a substrate, and the copolymer according to the above-described present invention on at least a part of the surface of the substrate.

3. A wetting agent comprising the copolymer according to the above-described present invention.

4. A method of wetting a medical device, the method comprising contacting the wetting agent according to the above-described present invention.

5. A method of producing a medical device, the method comprising the steps of: placing the wetting agent according to the above-described present invention and a substrate of a medical device in a vessel; and heat-treating the resultant.

The copolymer according to the present invention can suppress the reduction over time in lubricity of the surface of a medical device such as a contact lens, and therefore can be provided as a wetting agent comprising the copolymer. Further, the reduction over time in lubricity of a medical device having the copolymer on the surface is also suppressed.

DETAILED DESCRIPTION OF CERTAIN EMBODIMENTS OF THE INVENTION

Figure 1:
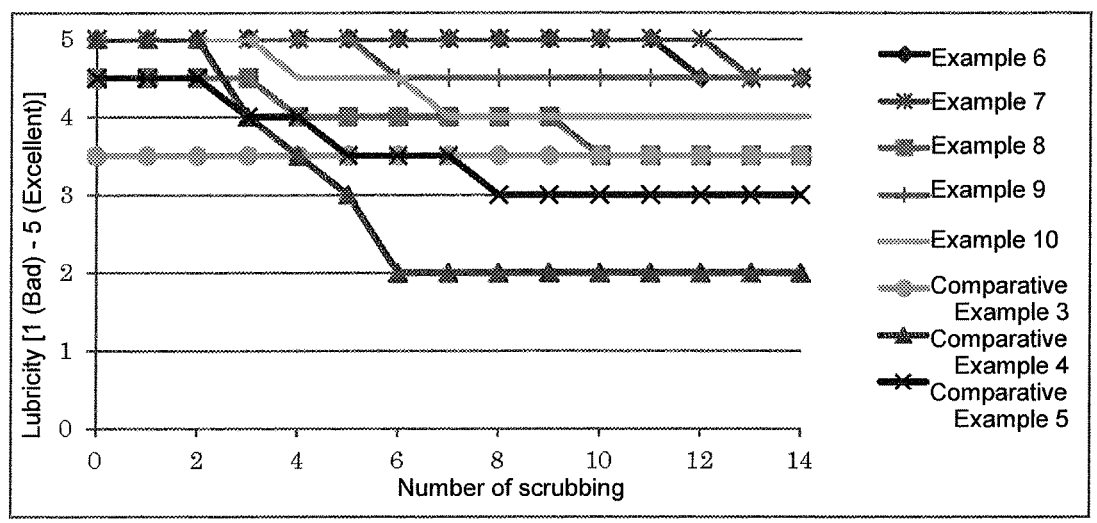
FIG. 1 shows the results of the test for the scrubbing durability of the surface-coated contact lenses produced in Examples 6 to 8 and Comparative Examples 3 to 5.

The copolymer of the present invention comprises as constitutional units: a monomer A containing a (meth)acryloyl group and an ester or amide structure in a molecule; and a monomer B containing a (meth)acrylamide group in the molecule and having a structure different from that of the monomer A. In the monomer A, the above ester or amide structure is not constituted by comprising a part of the above (meth)acryloyl group.

The term "(meth)acryloyl" as used herein represents both acryloyl and methacryloyl.

The term "(meth)acrylamide" as used herein represents both acrylamide and methacrylamide.

The monomer A is preferably a monomer containing a (meth)acryloyl group bound to an ester or amide structure via a divalent hydrocarbon group containing a hetero atom.

In the monomer A, the ester structure is not constituted by comprising a part of the above (meth)acryloyl group, but exists as a separate structure from the (meth)acryloyl group, and represents an acyloxy group. Examples thereof include $C_{1-10}$ linear or branched alkylcarbonyloxy groups such as acetoxy, propanoyloxy, butanoyloxy, 2-methylpropanoyloxy, pentanoyloxy, and 2,2-dimethylpropanoyloxy; $C_{3-10}$ cyclic alkylcarbonyloxy groups such as cyclopropylcarbonyloxy, cyclopentylcarbonyloxy, cyclohexylcarbonyloxy, and cycloheptylcarbonyloxy; and $C_{6-20}$ aromatic carbonyloxy groups such as benzoyloxy, 2-methylbenzoyloxy, 3-methylbenzoyloxy, 4-methylbenzoyloxy, 1-naphthoyloxy, and 2-naphthoyloxy.

In the monomer A, the amide structure is not constituted by comprising a part of the above (meth)acryloyl group, but exists as a separate structure from the (meth)acryloyl group, and preferably represents, in particular, acylamino, N-alkylacylamino or lactam. Examples thereof include $C_{1-10}$ acylamino groups such as acetylamino, propionylamino, butyrylamino, isobutyrylamino, valerylamino, isovalerylamino, and pivaloylamino; the above-described acylamino group substituted on its nitrogen atom with a $C_{1-6}$ alkyl group, such as N-methylacetylamino, N-ethylacetylamino, N-methylpropionylamino, N-ethylpropionylamino, and N-methylbutyrylamino; and lactam groups such as 2-oxopyrrolidin-1-yl, 2-oxopiperidin-1-yl, and 2-oxoazepan-1-yl. The amide structure may be a cyclic amide structure as shown in the formula [II] described later.

The term "hetero atom" represents an oxygen, nitrogen or sulfur atom, preferably oxygen or nitrogen atom.

In the present invention, examples of the above divalent hydrocarbon group include alkylene groups such as methylene, ethylene, propylene, and butylene; cycloalkylene groups such as 1,2-cyclopropylene, 1,3-cyclopentylene, 1,2-cyclohexylene, and 1,4-cyclohexylene; and arylene groups such as phenylene, and naphthylene. Thus, examples of the divalent hydrocarbon group containing a hetero atom include oxyalkylene groups such as oxymethylene (—$CH_2O$—), oxyethylene (—$CH_2CH_2O$—), oxypropylene (—$CH_2CH_2CH_2O$—), and oxybutylene (—$CH_2CH_2CH_2CH_2O$—); aminoalkylene groups such as aminomethylene (—$CH_2NH$—), aminoethylene (—$CH_2CH_2NH$—), aminopropylene (—$CH_2CH_2CH_2NH$—), and aminobutylene (—$CH_2CH_2CH_2CH_2NH$—); N-alkylamino alkylene groups such as N-methylaminomethylene (—$CH_2NCH_3$—), N-methylaminoethylene (—$CH_2CH_2NCH_3$—), N-methylaminopropylene (—$CH_2CH_2CH_2NCH_3$—), and N-methylaminobutylene (—$CH_2CH_2CH_2CH_2NCH_3$—); oxyarylene groups such as oxyphenylene, and oxynaphthylene; aminoarylene groups such as aminophenylene, and aminonaphthylene; and N-alkylamino arylene groups such as N-methylaminophenylene, and N-methylaminonaphthylene.

Examples of the monomers A include compounds having a structure represented by the following formula [I]:

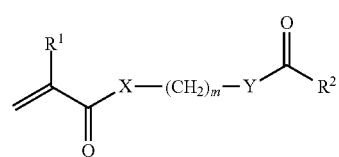

wherein,
$R^1$ represents hydrogen or methyl;
$R^2$ represents alkyl;
X represents oxygen or $NR^3$, wherein $R^3$ represents hydrogen or alkyl;
Y represents oxygen or $NR^4$, wherein $R^4$ represents hydrogen or alkyl;
$R^4$ and $R^2$ optionally together form a ring structure; and
m represents an integer from 1 to 4.

Among them, the monomer A having a more preferable structure is a compound represented by the following formula [II]:

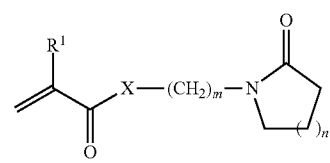

wherein,
$R^1$ represents hydrogen or methyl;
X represents oxygen or $NR^3$, wherein $R^3$ represents hydrogen or alkyl;
m represents an integer from 1 to 4; and
n represents an integer from 1 to 3.

$R^2$ may be linear or branched, and is preferably $C_{1-10}$ alkyl such as methyl, ethyl, propyl, 2-propyl, butyl, 2-butyl, tert-butyl, pentyl, 2-pentyl, 3-pentyl, hexyl, heptyl, and octyl.

When $R^3$ is alkyl, it may be linear or branched, and is preferably $C_{1-6}$ alkyl such as methyl, ethyl, propyl, 2-propyl, butyl, 2-butyl, tert-butyl, pentyl, 2-pentyl, 3-pentyl, and hexyl.

When $R^4$ is alkyl, it may be linear or branched, and is preferably $C_{1-6}$ alkyl such as methyl, ethyl, propyl, 2-propyl, butyl, 2-butyl, tert-butyl, pentyl, 2-pentyl, 3-pentyl, and hexyl.

When $R^4$ and $R^2$ together form a ring structure, $R^4$ may be linear or branched, and is preferably $C_{2-6}$ alkylene such as ethylene, propylene, butylene, and pentylene.

Specific examples of suitable monomers A include 2-acetoxyethyl (meth)acrylate, 2-(propionyloxy)ethyl (meth)acrylate, 2-(butyryloxy)ethyl (meth)acrylate, 2-(isobutyryloxy)ethyl (meth)acrylate, 2-(3-methylbutyryloxy)ethyl (meth)acrylate, 2-(pivaloyloxy)ethyl (meth)acrylate, 3-acetoxypropyl (meth)acrylate, 3-(propionyloxy)propyl (meth)acrylate, 3-(butyryloxy)propyl (meth)acrylate, 3-(isobutyryloxy)propyl (meth)acrylate, 3-(3-methylbutyryloxy)propyl (meth)acrylate, 3-(pivaloyloxy)propyl (meth)acrylate, 4-acetoxybutyl (meth)acrylate, 4-(propionyloxy)butyl (meth)acrylate, 4-(butyryloxy)butyl (meth)acrylate, 4-(isobutyryloxy)butyl (meth)acrylate, 4-(3-methylbutyryloxy)butyl (meth)acrylate, 4-(pivaloyloxy)butyl (meth)acrylate, 2-acetamidoethyl (meth)acrylate, 2-propionamidoethyl (meth)acrylate, 2-butylamidoethyl (meth)acrylate, 2-isobutylamidoethyl (meth)acrylate, 2-(3-methylbutanamido)ethyl (meth)acrylate, 2-pivalamidoethyl (meth)acrylate, 3-acetamidopropyl (meth)acrylate, 3-propionamidopropyl (meth)acrylate, 3-butylamidopropyl (meth)acrylate, 3-isobutylamidopropyl (meth)acrylate, 3-(3-methylbutanamido)propyl (meth)acrylate, 3-pivalamidopropyl (meth)acrylate, 4-acetamidobutyl (meth)acrylate, 4-propionamidobutyl (meth)acrylate, 4-butylamidobutyl (meth)acrylate, 4-isobutylamidobutyl (meth)acrylate, 4-(3-methylbutanamido)butyl (meth)acrylate, 4-pivalamidobutyl (meth)acrylate, 2-(2-oxopyrrolidin-1-yl)ethyl (meth)acrylate, 2-(2-oxopiperidin-1-yl)ethyl (meth)acrylate, 2-(2-oxoazepan-1-yl)ethyl (meth)acrylate, 3-(2-oxopyrrolidin-1-yl)propyl (meth)acrylate, 3-(2-oxopiperidin-1-yl)propyl (meth)acrylate, 3-(2-oxoazepan-1-yl)propyl (meth)acrylate, 4-(2-oxopyrrolidin-1-yl)butyl (meth)acrylate, 4-(2-oxopiperidin-1-yl)butyl (meth)acrylate, 4-(2-oxoazepan-1-yl)butyl (meth)acrylate, N-(2-acetoxyethyl)(meth)acrylamide, N-(2-(propionyloxy)ethyl)(meth)acrylamide, N-(2-(butyryloxy)ethyl)(meth)acrylamide, N-(2-(isobutyryloxy)ethyl)(meth)acrylamide, N-(2-(3-methylbutyryloxy)ethyl)(meth)acrylamide, N-(2-(pivaloyloxy)ethyl)(meth)acrylamide, N-(3-acetoxypropyl)(meth)acrylamide, N-(3-(propionyloxy)propyl)(meth)acrylamide, N-(3-(butyryloxy)propyl)(meth)acrylamide, N-(3-(isobutyryloxy)propyl)(meth)acrylamide, N-(3-(3-methylbutyryloxy)propyl)(meth)acrylamide, N-(3-(pivaloyloxy)propyl)(meth)acrylamide, N-(4-acetoxybutyl)(meth)acrylamide, N-(4-(propionyloxy)butyl)(meth)acrylamide, N-(4-(butyryloxy)butyl)(meth)acrylamide, N-(4-(isobutyryloxy)butyl)(meth)acrylamide, N-(4-(3-methylbutyryloxy)butyl)(meth)acrylamide, N-(4-(pivaloyloxy)butyl)(meth)acrylamide, N-(2-acetamidoethyl)(meth)acrylamide, N-(2-propionamidoethyl)(meth)acrylamide, N-(2-butylamidoethyl)(meth)acrylamide, N-(2-isobutylamidoethyl)(meth)acrylamide, N-(2-(3-methylbutanamido)ethyl)(meth)acrylamide, N-(2-pivalamidoethyl)(meth)acrylamide, N-(3-acetamidopropyl)(meth)acrylamide, N-(3-propionamidopropyl)(meth)acrylamide, N-(3-butylamidopropyl)(meth)acrylamide, N-(3-isobutylamidopropyl)(meth)acrylamide, N-(3-(3-methylbutanamido)propyl)(meth)acrylamide, N-(3-pivalamidopropyl)(meth)acrylamide, N-(4-acetamidobutyl)(meth)acrylamide, N-(4-propionamidobutyl)(meth)acrylamide, N-(4-butylamidobutyl)(meth)acrylamide, N-(4-isobutylamidobutyl)(meth)acrylamide, N-(4-(3-methylbutanamido)butyl)(meth)acrylamide, N-(4-pivalamidobutyl)(meth)acrylamide, N-(2-(2-oxopyrrolidin-1-yl)ethyl)(meth)acrylamide, N-(2-(2-oxopiperidin-1-yl)ethyl)(meth)acrylamide, N-(2-(2-oxoazepan-1-yl)ethyl)(meth)acrylamide, N-(3-(2-oxopyrrolidin-1-yl)propyl)(meth)acrylamide, N-(3-(2-oxopiperidin-1-yl)propyl)(meth)acrylamide, N-(3-(2-oxoazepan-1-yl)propyl)(meth)acrylamide, N-(4-(2-oxopyrrolidin-1-yl)butyl)(meth)acrylamide, N-(4-(2-oxopiperidin-1-yl)butyl)(meth)acrylamide, and N-(4-(2-oxoazepan-1-yl)butyl)(meth)acrylamide. Among them, monomers A having a nitrogen atom as Y in formula [I] are preferable from the viewpoint of keeping higher hydrophilicity. Examples of such a monomer A include 2-acetamidoethyl (meth)acrylate, 2-propionamidoethyl (meth)acrylate, 2-butylamidoethyl (meth)acrylate, 2-isobutylamidoethyl (meth)acrylate, 2-(3-methylbutanamido)ethyl (meth)acrylate, 2-pivalamidoethyl (meth)acrylate, 3-acetamidopropyl (meth)acrylate, 3-propionamidopropyl (meth)acrylate, 3-butylamidopropyl (meth)acrylate, 3-isobutylamidopropyl (meth)acrylate, 3-(3-methylbutanamido)propyl (meth)acrylate, 3-pivalamidopropyl (meth)acrylate, 4-acetamidobutyl (meth)acrylate, 4-propionamidobutyl (meth)acrylate, 4-butylamidobutyl (meth)acrylate, 4-isobutylamidobutyl (meth)acrylate, 4-(3-methylbutanamido)butyl (meth)acrylate, 4-pivalamidobutyl (meth)acrylate, 2-(2-oxopyrrolidin-1-yl)ethyl (meth)acrylate, 2-(2-oxopiperidin-1-yl)ethyl (meth)acrylate, 2-(2-oxoazepan-1-yl)ethyl (meth)acrylate, 3-(2-oxopyrrolidin-1-yl)propyl (meth)acrylate, 3-(2-oxopiperidin-1-yl)propyl (meth)acrylate, 3-(2-oxoazepan-1-yl)propyl (meth)acrylate, 4-(2-oxopyrrolidin-1-yl)butyl (meth)acrylate, 4-(2-oxopiperidin-1-yl)butyl (meth)acrylate, 4-(2-oxoazepan-1-yl)butyl (meth)acrylate, N-(2-acetamidoethyl)(meth)acrylamide, N-(2-propionamidoethyl)(meth)acrylamide, N-(2-butylamidoethyl)(meth)acrylamide, N-(2-isobutylamidoethyl)(meth)acrylamide, N-(2-(3-methylbutanamido)ethyl)(meth)acrylamide, N-(2-pivalamidoethyl)(meth)acrylamide, N-(3-acetamidopropyl)(meth)acrylamide, N-(3-propionamidopropyl)(meth)acrylamide, N-(3-butylamidopropyl)(meth)acrylamide, N-(3-isobutylamidopropyl)(meth)acrylamide, N-(3-(3-methylbutanamido)propyl)(meth)acrylamide, N-(3-pivalamidopropyl)(meth)acrylamide, N-(4-acetamidobutyl)(meth)acrylamide, N-(4-propionamidobutyl)(meth)acrylamide, N-(4-butylamidobutyl)(meth)acrylamide, N-(4-isobutylamidobutyl)(meth)acrylamide, N-(4-(3-methylbutanamido)butyl)(meth)acrylamide, N-(4-pivalamidobutyl)(meth)acrylamide, N-(2-(2-oxopyrrolidin-1-yl)ethyl)(meth)acrylamide, N-(2-(2-oxopiperidin-1-yl)ethyl)(meth)acrylamide, N-(2-(2-oxoazepan-1-yl)ethyl)(meth)acrylamide, N-(3-(2-oxopyrrolidin-1-yl)propyl)(meth)acrylamide, N-(3-(2-oxopiperidin-1-yl)propyl)(meth)acrylamide, N-(3-(2-oxoazepan-1-yl)propyl)(meth)acrylamide, N-(4-(2-oxopyrrolidin-1-yl)butyl)(meth)acrylamide, N-(4-(2-oxopiperidin-1-yl)butyl)(meth)acrylamide, and N-(4-(2-oxoazepan-1-yl)butyl)(meth)acrylamide. Among them, monomers A in which m is 2 or less in formula [I] are preferable from the viewpoint of having a high hydrophilicity. Examples of such a monomer A include 2-acetamidoethyl (meth)acrylate, 2-propionamidoethyl (meth)acrylate, 2-butylamidoethyl (meth)acrylate, 2-isobutylamidoethyl (meth)acrylate, 2-(3-methylbutanamido)ethyl (meth)acrylate, 2-pivalamidoethyl (meth)acrylate, 2-(2-oxopyrrolidin-1-yl)ethyl (meth)acrylate, 2-(2-oxopiperidin-1-yl)ethyl (meth)acrylate, 2-(2-oxoazepan-1-yl)ethyl (meth)acrylate, N-(2-acetamidoethyl)(meth)acrylamide, N-(2-propionamidoethyl)(meth)acrylamide, N-(2-butylamidoethyl)(meth)acrylamide, N-(2-isobutylamidoethyl)(meth)acrylamide, N-(2-(3-methylbutanamido)ethyl)(meth)acrylamide, N-(2-pivalamidoethyl)(meth)acrylamide, N-(2-(2-oxopyrrolidin-1-yl)ethyl)(meth)acrylamide, N-(2-(2-oxopiperidin-1-yl)ethyl)(meth)acrylamide, and N-(2-(2-oxoazepan-1-yl)ethyl)(meth)acrylamide. Among them, monomers A in which n is 1 in formula [II] such as 2-(2-oxopyrrolidin-1-yl)ethyl (meth)acrylate and N-(2-(2-oxopyrrolidin-1-yl)ethyl)(meth)acrylamide are most preferred from the viewpoint of having a high hydrophilicity. The monomer A can be used individually or two or more of them can be used in combination.

The monomer B is a compound containing a (meth)acrylamide group in a molecule; and having a structure different from that of the monomer A; preferably being hydrophilic; and preferably having a structure specifically represented by the following formula [III]:

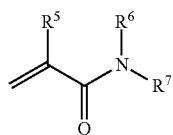

wherein,
$R^5$ represents hydrogen or methyl; and
$R^6$ and $R^7$ each independently represent hydrogen or alkyl; or $R^6$ and $R^7$ optionally together form a ring structure.

When one of $R^6$ and $R^7$ is hydrogen, the other preferably is alkyl.

When $R^6$ and/or $R^7$ each represent alkyl, it may be linear or branched, and is preferably $C_{1-6}$ alkyl, such as methyl, ethyl, propyl, 2-propyl, butyl, 2-butyl, tert-butyl, pentyl, 2-pentyl, 3-pentyl, and hexyl.

When $R^6$ and $R^7$ together form a ring structure, $R^6$—$R^7$ formed by the binding of $R^6$ and $R^7$ may be linear or branched, and is preferably $C_{2-6}$ alkylene, such as ethylene, 1,2-propylene, 1,3-propylene, 1,2-butylene, 1,3-butylene, 1,4-butylene, and 1,5-pentylene.

The term "monomer is hydrophilic", as described above, means that the solubility of the monomer in water or a borate buffer solution at 25° C. is 0.1% by mass or more. The solubility is more preferably 1.0% by mass or more, and still more preferably 10% by mass or more.

The borate buffer solution used in the present invention refers to an aqueous solution prepared by dissolving 8.48 g of sodium chloride, 9.26 g of boric acid, 1.0 g of sodium borate (sodium tetraborate decahydrate) and 0.10 g of ethylenediaminetetraacetic acid in pure water to a volume of 1 L. The aqueous solution may have a different volume as long as the mixing ratio is the same.

Specific examples of suitable monomer B include N-methyl(meth)acrylamide, N-ethyl(meth)acrylamide, N-propyl(meth)acrylamide, N-butyl(meth)acrylamide, N,N-dimethyl (meth)acrylamide, N-ethyl-N-methyl(meth)acrylamide, N-methyl-N-propyl(meth)acrylamide, N-butyl-N-methyl(meth)acrylamide, N,N-diethyl(meth)acrylamide, N-ethyl-N-propyl(meth)acrylamide, N-butyl-N-ethyl(meth)acrylamide, 1-(meth)acryloylpyrrolidine, and 1-(meth)acryloylpiperidine. Among them, monomers B in which $R^6$ and/or $R^7$ has(have) 3 or less carbon atoms are preferable from the viewpoint of having higher hydrophilicity. Examples of such a monomer B include N-methyl(meth)acrylamide, N-ethyl(meth)acrylamide, N-propyl(meth)acrylamide, N,N-dimethyl(meth)acrylamide, N-ethyl-N-methyl(meth)acrylamide, N-methyl-N-propyl(meth)acrylamide, N,N-diethyl(meth)acrylamide, N-ethyl-N-propyl(meth)acrylamide, and 1-(meth)acryloylpiperidine. Among them, monomers B in which the total number of carbon atoms of $R^6$ and $R^7$ is 2 or less are preferable, and most preferred are N-methyl(meth)acrylamide, N-ethyl(meth)acrylamide, and N,N-dimethyl(meth)acrylamide. The monomer B can be used individually, or two or more monomers B can be used in combination.

The copolymer of the present invention comprises as constitutional units the above-mentioned monomers A and B. The copolymer may be linear or branched, and may be a random copolymer, an alternating copolymer, a block copolymer or a graft copolymer, but is not particularly limited thereto.

The copolymer of the present invention is preferably water-soluble. The term "water-soluble" means that the solubility in water or a borate buffer solution at 25° C. is 0.1% by mass or more. The solubility is more preferably 1.0% by mass or more, and still more preferably 10% by mass or more. The maximum solubility is usually, but not particularly limited to, 50% by mass or less. The aqueous solution dissolving such a water-soluble copolymer is a transparent solution, and not an emulsion (dispersion). The copolymer which is not water-soluble is not preferred, because it may not be able to uniformly coat the surface of a medical device as a wetting agent.

The copolymer of the present invention may be dissolved in water to obtain an aqueous solution or may be added to an aqueous solution previously prepared. Examples of the aqueous solution before dissolution of such a copolymer includes, but is not limited to, saline, other buffers and deionized water. A preferred aqueous solution is a saline solution containing a salt. Examples of the salt include, but are not limited to, sodium chloride, sodium borate, sodium phosphate, sodium hydrogenphosphate, and sodium dihydrogenphosphate, as well as the corresponding potassium salts of the acids. Since these components usually form a buffer containing an acid and its conjugate base by mixing, only a relatively small change in pH occurs when an acid or base is added to the aqueous solution. The buffer may further contain, for example, 2-(N-morpholino)ethanesulfonic acid (MES), sodium hydroxide, 2,2-bis(hydroxymethyl)-2,2',2"-nitrilotriethanol, N-tris(hydroxymethyl)methyl-2-aminoethanesulfonic acid, citric acid, sodium citrate, sodium carbonate, sodium hydrogen carbonate, acetic acid, sodium acetate, and ethylenediaminetetraacetic acid, and combinations thereof. Preferably, the solution is a borate buffered physiological saline solution (the same as the above borate buffer solution) or a phosphate buffered physiological saline solution.

The contents of the monomers A and B in the copolymer of the present invention are, but not particularly limited thereto, 5 to 50 mol % for the monomer A and 50 to 95 mol % for the monomer B. The content of the monomer A is more preferably 5 to 35 mol %, and the content of the monomer B is more preferably 65 to 95 mol %. Any combination of the numerical values of the above-described upper limit and lower limit may be employed.

The copolymer of the present invention can be produced by polymerizing the above-described monomers A and B. When producing the copolymer of the present invention by the polymerization, a polymerization initiator may be added to accelerate the polymerization. Examples of suitable initiators include thermal polymerization initiators such as peroxides and azo compounds, photopolymerization initiators (which may be for ultraviolet light, visible light or a combination thereof) or mixtures thereof. When performing thermal polymerization, a thermal polymerization initiator having an optimum decomposition profile for a desired reaction temperature is selected and used. Generally, azo initiators or peroxide initiators with a 10-hour half-life temperature of 40° C. to 120° C. are preferred. Examples of the photopolymerization initiators include carbonyl compounds, peroxides, azo compounds, sulfur compounds, halogen compounds, and metal salts.

Specific examples of the thermal polymerization initiator include 2,2'-azobis(isobutyronitrile) (AIBN), 2,2'-azobis(2-methylbutyronitrile), 2,2'-azobis(2,4-dimethylvaleronitrile), 1,1'-azobis(cyclohexane-1-carbonitrile), 2,2'-azobis[2-(2-imidazolin-2-yl)propane], 2,2'-azobis(2-amidinopropane)dihydrochloride, 2,2'-azobis[N-(2-carboxyethyl)-2-methylpropionamidine], 2,2'-azobis[2-methyl-N-(2-hydroxyethyl)propionamido], 2,2'-azobis(N-butyl-2-methylpropionamide), dimethyl 2,2'-azobis(2-methylpropionate), 4,4'-azobis(4-cyanovaleric acid), tert-butylhydroperoxide, cumene hydroperoxide, di-tert-butyl peroxide, and benzoyl peroxide. Among them, from the viewpoint of being soluble in organic solvents, preferably used are 2,2'-azobis(isobutyronitrile) (AIBN), 2,2'-azobis(2-methylbutyronitrile), 2,2'-azobis(2,4-dimethylvaleronitrile), 1,1'-azobis(cyclohexane-1-carbonitrile), 2,2'-azobis[2-(2-imidazolin-2-yl)propane], 2,2'-azobis[2-methyl-N-(2-hydroxyethyl)propionamido], 2,2'-azobis(N-butyl-2-methylpropionamide), dimethyl 2,2'-azobis(2-methylpropionate), 4,4'-azobis(4-cyanovaleric acid), tert-butylhydroperoxide, cumene hydroperoxide, di-tert-butyl peroxide, and benzoyl peroxide.

Examples of the photopolymerization initiator include aromatic α-hydroxyketone, alkoxyoxybenzoin, acetophenone, acylphosphineoxide, bisacylphosphineoxide, and tertiary amine plus diketone, and mixtures thereof. More specific examples include 1-hydroxycyclohexyl phenyl ketone, 2-hydroxy-2-methyl-1-phenyl-propan-1-on, bis(2,6-dimethoxybenzoyl)-2,4,4-trimethylpentylphosphineoxide (DMBAPO), bis(2,4,6-trimethylbenzoyl)phenylphosphineoxide ("IRGACURE" (registered trademark) 819), 2,4,6-trimethylbenzyldiphenylphosphineoxide, 2,4,6-trimethylbenzoyldiphenylphosphineoxide, benzoin methyl ether, and a combination of camphorquinone and ethyl 4-(N,N-dimethylamino)benzoate.

Examples of commercially available visible light polymerization initiators include "IRGACURE" (registered trademark) 819, "IRGACURE" (registered trademark) 1700, "IRGACURE" (registered trademark) 1800, "IRGACURE" (registered trademark) 1850 (all manufactured by BASF), and Lucirin TPO initiator (manufactured by BASF). Examples of commercially available UV light polymerization initiators include "DAROCUR" (registered trademark) 1173 and "DAROCUR" (registered trademark) 2959 (manufactured by BASF).

These polymerization initiators may be used individually or in combination. The amount of the polymerization initiator to be used should be appropriately adjusted depending on the target molecular weight of the copolymer to be obtained. If the amount is too small, polymerization will not start, whereas if it is too much, molecular weight tends to be low, and recombination is likely to be stopped, making it difficult to obtain a polymer with a desired molecular weight. Therefore, the amount of the polymerization initiator to be used is preferably in the range of 0.01% by mass to 5% by mass relative to the polymerization mixture.

The polymerization mixture refers to a reaction solution containing the monomers used in polymerization, and refers to a solution containing monomers to be polymerized, a polymerization solvent, and a polymerization initiator. The polymerization mixture may contain a chain transfer agent. Preferred examples of the chain transfer agent include mercaptans such as hydroxyethylmercaptan, lauryl mercaptan, and n-dodecylmercaptan; α-methylstyrene dimer, and limonene.

When the copolymer of the present invention is prepared by polymerization, a polymerization solvent can be used. The solvent may be either an organic or inorganic solvent. Examples of the solvent include water; alcohol solvents such as methanol, ethanol, propanol, 2-propanol, butanol, 2-butanol, tert-butylalcohol, tert-amyl alcohol, 3,7-dimethyl-3-octanol, ethylene glycol, diethylene glycol, triethylene glycol, tetraethylene glycol and polyethylene glycol; aromatic hydrocarbon solvents such as benzene, toluene and xylene; aliphatic hydrocarbon solvents such as hexane, heptane, octane, decane, petroleum ether, kerosene, ligroin and paraffin; alicyclic hydrocarbon solvents such as cyclopentane, cyclohexane and ethylcyclohexane; ketone solvents such as acetone, methyl ethyl ketone and methyl isobutyl ketone; ester solvents such as ethyl acetate, butyl acetate, amyl acetate, ethyl lactate, methyl benzoate and ethylene glycol diacetate; and ether solvents such as diethyl ether, tert-butyl methyl ether, tetrahydrofuran, dioxane, ethylene glycol dimethyl ether, diethylene glycol dimethyl ether, triethylene glycol dimethyl ether, tetraethylene glycol dimethyl ether and polyethylene glycol dimethyl ether. These solvents can be used individually or in combination. Among them, water, tert-butyl alcohol, tert-amyl alcohol, 3,7-dimethyl-3-octanol are preferably used from the viewpoint that they hardly inhibit radical polymerization.

When a polymerization solvent is used, if the monomer concentration in the polymerization mixture is too low, a sufficient molecular weight cannot be achieved, whereas if it is too high, there is a risk of thermal runaway polymerization. Therefore, the monomer concentration is preferably from 10% by mass to 80% by mass, more preferably 15% by mass to 65% by mass, most preferably 20% by mass to 50% by mass. The range may be defined by any combination of the above-described upper limits and lower limits.

The copolymer obtained by the method of the present invention may be purified by using conventional means for polymer isolation, for example, distillation, column chromatography, precipitation, washing with a solvent in which the copolymer is insoluble, and GPC fractionation.

A copolymer of the present invention having an excessively low mass average molecular weight may result in insufficient lubricity. On the other hand, a copolymer having an excessively high mass average molecular weight may result in a solution containing the copolymer whose viscosity is too high and ease of handling may be lost. From the viewpoint of lubricity and ease of handling, the mass average molecular weight of the copolymer is preferably from 5,000 to 5,000,000 daltons, more preferably from 50,000 to 3,000,000 daltons, still more preferably 80,000 to 1,000,000 daltons. The range may be defined by any combination of the above-described upper limits and lower limits.

The copolymer of the present invention can be used for imparting lubricity to plastic molded articles such as medical devices and films, and in particular can be suitably used for medical devices.

Examples of the medical device include ophthalmic lens, endoscope, catheter, infusion tube, gas transportation tube, stent, sheath, cuff, tube connector, access port, drainage bag, blood circuit, wound dressing, implant and various drug carriers. Among them, ophthalmic lens is preferred. Examples of the ophthalmic lens include contact lenses such as soft contact lenses, hard contact lenses, and hybrid contact lenses; scleral lenses, intraocular lenses, artificial corneas, cornea inlays, corneal onlays, and glass lenses.

When the medical device is an ophthalmic lens, it is preferably a contact lens, more preferably a soft contact lens, still more preferably a hydrogel soft contact lens, particularly preferably a HEMA soft contact lens.

The medical device of the present invention has the above-mentioned copolymer comprising the above-mentioned monomers A and B as constitutional units on at least a part of the surface of a substrate constituting the medical device. The substrate constituting such medical devices may also be obtained through preparation of a copolymer formed by mixing hydrophilic compounds, examples of which include (meth)acrylamides such as N,N-dimethylacrylamide; N-vinylamides such as N-vinylpyrrolidone; hydroxyalkyl (meth)acrylates and alkyl ethers thereof such as 2-hydroxyethyl (meth)acrylate, and 2-methoxyethyl (meth) acrylate; and polyethylene glycol mono(meth)acrylates and methyl ethers thereof such as diethylene glycol mono(meth) acrylate, and diethylene glycol mono(meth)acrylate methyl ether; and, as necessary, crosslinking compounds, examples of which include di(meth)acrylates such as polyethylene glycol di(meth)acrylate, N,N-methylene bisacrylamide, and polyfunctional (meth)acrylate. When making the medical device have a low water content, alkyl (meth)acrylates such as butyl acrylate and ethylhexyl acrylate may also be used in the silicon-containing compound.

The copolymer of the present invention exists on the surface of the substrate by virtue of at least one of covalent binding, hydrogen binding, electrostatic interaction, hydrophobic interaction, chain entanglement, and van der Waals force, and a part of the copolymer may infiltrate into the interior of the substrate. These interactions stabilize the copolymer near the surface of the substrate and improve the lubricity of the medical device. When the medical device is an ophthalmic lens, especially a contact lens, improvement in lubricity works advantageously for comfortable wearing feeling.

From the viewpoint of improving the compatibility of the medical device of the present invention to a living body and smoothing movement of the medical device in contact with the surface of a body tissue, and particularly when the medical device is a contact lens according to one aspect of the present invention, from the viewpoint of preventing the contact lens from sticking to the cornea of the wearer, the surface of the medical device preferably has an excellent lubricity. As an indicator of lubricity, a smaller coefficient of dynamic friction as measured by the method described in Example herein is preferred. A smaller coefficient of dynamic friction produces a smaller frictional force, and as a result the influence on a living body (e.g., cornea and palpebral conjunctiva in the case of a contact lens) when frictions occur against the living body is reduced. The coefficient of dynamic friction preferably is 0.2 or less. However, since extremely small frictions tend to result in difficulty with handling during wearing and removing, it is preferable that the coefficient of dynamic friction is 0.01 or more. The coefficient of dynamic friction is measured with respect to the glass surface using a sample in a state wetted with a borate buffer solution.

When the surface of a medical device is coated with the copolymer of the present invention, the wettability of the device surface can be determined by using a known method for measuring contact angle (i.e., sessile drop method, captive bubble method or dynamic contact angle method). As an indicator of wettability, a smaller contact angle hysteresis (DCA hysteresis) as measured by the method described later in Example herein is preferred. The DCA hysteresis is preferably 8° or smaller, more preferably 6° or smaller, particularly preferably 5° or smaller. The lower limit is preferably 0°. However, since this may be difficult to achieve in practice, it is satisfactory if the lower limit is 0.5°. The range may be defined by any combination of the above-described upper limits and lower limits.

The wetting agent of the present invention comprises the above-mentioned copolymer of the present invention and can bind to the surface of and/or infiltrate into the substrate by the above-described interaction.

The wetting agent means a surfactant that increases the action of making the solid surface wettable. As the wetting agent, a polymer which gives lubricity to the surface of a medical device is preferable, and a polymer which gives lubricity to the surface of an ophthalmic lens is more preferable.

The external wetting agent means a type of wetting agents, for example, a wetting agent for coating the surface of a medical device by physical contact with the surface of the medical device.

The wetting agent may be in the form of any aqueous solution used for preserving the medical device. Examples of the medium for the aqueous solution include, but are not limited to, saline, other buffers and deionized water. A preferred aqueous solution is a saline solution containing a salt, examples of which include, but are not limited to, sodium chloride, sodium borate, sodium phosphate, sodium hydrogenphosphate, sodium dihydrogenphosphate, and corresponding potassium salts of the acids. Since these components usually form a buffer containing an acid and its conjugate base by mixing, only a relatively small change in pH occurs even when an acid or base is added to the aqueous solution. The buffer may further contain, for example, 2-(N-morpholino)ethanesulfonic acid (MES), sodium hydroxide, 2,2-bis(hydroxymethyl)-2,2',2"-nitrilotriethanol, N-tris(hydroxymethyl)methyl-2-aminoethanesulfonic acid, citric acid, sodium citrate, sodium carbonate, sodium hydrogen carbonate, acetic acid, sodium acetate, or ethylenediaminetetraacetic acid, or a combination thereof. Preferably, the solution is a borate buffered saline solution or a phosphate buffered saline solution. The solution may also contain a known additional ingredient such as a viscosity modifier, antimicrobial agent, polyelectrolyte, stabilizer, chelating agent, antioxidant, or a combination thereof at a concentration that does not adversely affect the effect of the present invention.

By physically contacting the wetting agent comprising the copolymer of the present invention with the surface of a medical device, the surface of the medical device can be coated, thereby wetting the medical device. Thus, the surface of a medical device such as an ophthalmic lens can be coated by placing the wetting agent and a medical device substrate in a vessel and heat treating them.

When the medical device is an ophthalmic lens, examples of suitable heat treatment include heating at a temperature ranging from 40° C. to 150° C. for 10 minutes to 60 minutes, and include particularly preferably a conventional heat sterilization cycle carried out at a temperature of about 120° C. for about 30 minutes. However, the heat treatment is not limited thereto and the heat treatment may be carried out in an autoclave. When the heat sterilization is not employed, wrapped lenses may be individually heat treated. Suitable temperatures for the individual heat treatment include at least about 40° C. or higher, preferably about 80° C. or higher. Suitable times for the heat treatment include at least about 10 minutes, preferably 10 minutes to 1 hour. A higher temperature allows a shorter time for heat treatment.

EXAMPLES

The present invention will now be described in detail with reference to examples below, but is not limited thereto.
Analysis and Evaluation Methods
(1) Determination of Molecular Weight of Polymer Prominence GPC system (Shimadzu Corporation) was used for measurement. The system comprises the following: pump: LC-20AD, autosampler: SIL-20AHT, column oven: CTO-20A, detector: RID-10A, column: Tosoh GMPWXL (inner diameter 7.8 mm×30 cm, particle diameter 13 μm). Measurement was carried out using water/methanol=1/1 (0.1 N lithium nitrate was added) as an eluting solvent at a flow rate of 0.5 mL/min and a measurement time of 30 minutes. The sample concentration was 0.2% by mass, and the sample amount injected was 20 μL. Calibration curves were determined using PEG/PEO standard samples (0.1 kD to 1258 kD) manufactured by Agilent.
(2) Lubricity and Scrubbing Durability After steam sterilization, the contact lens was removed from the packaging solution and rubbed with human fingers five times, and a five-point sensory evaluation was carried out. The score was taken as the lubricity at the 0th cycle (initial lubricity). As criteria of the lubricity at this time, commercially available contact lens "2-Week ACUVUE" (registered trademark) (manufactured by J & J) was ranked 3 in the 5-point evaluation, and "ACUVUE" (registered trademark) and "OASYS" (registered trademark) (manufactured by J & J) were ranked 5 in the 5-point evaluation.

Further, the sample after the above evaluation was manipulated as follows: placing the sample in a recess in the center of a palm; adding a washing solution ("OPTI-FREE" (registered trademark) (manufactured by Alcon Japan) thereto; rubbing the front and back surfaces of the sample ten times with the ball of an index finger of the other hand; and washing the sample well with water. The above manipulations as one cycle were repeated 14 cycles. Thereafter, the sample was washed with pure water and immersed in a phosphate buffer solution. Sensory evaluations in the 1st to 14th cycles were carried out based on the following five-point scale. FIG. 1 shows the evaluation results from 14 cycles.
5: Excellent lubricity
4: Intermediate lubricity between 5 and 3
3: Moderate lubricity
2: Almost no lubricity (between 3 and 1)
1: No lubricity
(3) Measurement of Coefficient of Dynamic Friction Measurement was carried out using KE-SE-STP friction tester manufactured by Kato Tech. A clean glass plate cleaned well was placed on the stage of the friction tester and three contact lenses were placed on the glass plate at even intervals on the circumference using a measurement adapter dedicated to contact lenses. The contact lenses were brought into contact with the glass surface via a droplet of 0.1 mL of borate buffer solution, and the measurement adapter was moved at a speed of 2.0 mm/second under a 87 g of static load, and the coefficient of dynamic friction of the surface was measured.
(4) Measurement of Dynamic Contact Angle After steam sterilization, a contact lens was removed from the packaging solution and cut out as a rectangular sample with a width of 5 mm. The thickness of the outer edge portion of the lens was measured. Then, the sample was immersed in a borate buffer solution and subjected to ultrasonic cleaning for 20 seconds. The dynamic contact angle with respect to the borate buffer solution was measured using a WET-6000 dynamic contact angle meter manufactured by Rhesca. Forward (a motion for immersing the sample in the borate buffer solution) and backward (a motion for completely remove the sample immersed from the borate buffer solution) movements of the sample were defined as one cycle, and the dynamic contact angles at the second cycle when two cycles were performed were compared (immersion speed: 7 mm/min). The difference between the values of the second forward and backward movements (DCA hysteresis), which is an index representing the smoothness and molecular orientation of the sample surface, was also calculated.
(5) Measurement of NMR Measurement was carried out using JNM-EX270 nuclear magnetic resonance apparatus (JEOL). $^1$H-NMR was measured using as a measurement sample a solution prepared by dissolving about 5 mg of a compound to be measured in about 0.6 mL of deuterated solvent (deuterated chloroform).

Synthesis of Monomers

Reference Example 1

Synthesis of 2-(2-oxopyrrolidin-1-yl)ethyl Acrylate (VPA)

A 500 mL three-necked flask equipped with a condenser, a dropping funnel and a calcium chloride tube was charged with 2-hydroxyethyl pyrrolidone (manufactured by Tokyo Chemical Industry, 51.68 g, 400.1 mmol), ethyl acetate (manufactured by Wako Pure Chemical, 250 mL), and triethylamine (manufactured by Wako Pure Chemical, 44.46 g, 439.4 mmol) under a nitrogen gas flow. After cooling the mixed solution to 10° C., a solution of acryloyl chloride (manufactured by Tokyo Chemical Industry, 38.03 g, 420.2 mmol) diluted with ethyl acetate (manufactured by Wako Pure Chemical, 50 mL) was added dropwise over 80 minutes. The mixture was then allowed to warm to room temperature and stirred for another 2 hours. After completion of stirring, triethylamine hydrochloride was removed by filtration, and the solvent was distilled off with an evaporator. Then, the residue was purified by distillation under reduced pressure (146° C., 0.05 mmHg) to obtain 12.67 g of a compound (VPA) as a colorless liquid.

$^1$H-NMR (CDCl$_3$) δ ppm 1.96 (2H, m, NCH$_2$CH$_2$CH$_{2=0}$), 2.30 (2H, t, NCH$_2$CH$_2$CH$_{2=0}$), 3.40 (2H, t, NCH$_2$CH$_2$CH$_{2=0}$), 3.54 (2H, t, NCH$_2$CH$_2$OCO), 4.22 (2H, t, NCH$_2$CH$_2$OCO), 5.78, 6.04, 6.32 (each 1H, dd, CH$_2$=CHCOO)

Reference Example 2

Synthesis of 2-acetoxyethyl Acrylate (AcEA)

A 500 mL three-necked flask equipped with a condenser, a dropping funnel and a calcium chloride tube was charged with 2-hydroxyethyl acetate (manufactured by Tokyo Chemical Industry, 27.74 g, 266.4 mmol), ethyl acetate (manufactured by Wako Pure Chemical, 260 mL), and triethylamine (manufactured by Wako Pure Chemical, 29.65 g, 293.1 mmol) under a nitrogen gas flow and cooled to 10° C. To the mixed solution, was added a solution of acryloyl chloride (manufactured by Tokyo Chemical Industry, 25.31 g, 279.8 mmol) diluted with ethyl acetate (manufactured by Wako Pure Chemical, 50 mL) dropwise over 80 minutes. The mixture was then allowed to warm to room temperature and stirred for another 2 hours. After completion of stirring, the procedures according to Reference Example 1 were carried out to obtain 12.41 g of the desired product (AcEA) as a colorless liquid.

$^1$H-NMR (CDCl$_3$) δ ppm 2.05 (3H, s, OCOCH$_3$), 4.31 (4H, m, CH$_3$COOCH$_2$CH$_2$O), 5.83, 6.11, 6.41 (each 1H, dd, CH$_2$=CHCOO)

Reference Example 3

Synthesis of 2-acetamidoethyl Acrylate (AmEA)

A 500 mL three-necked flask equipped with a condenser, a dropping funnel and a calcium chloride tube was charged with 2-hydroxyethyl acetamide (manufactured by Tokyo Chemical Industry, 24.45 g, 237.1 mmol), ethyl acetate (manufactured by Wako Pure Chemical, 250 mL), and triethylamine (manufactured by Wako Pure Chemical, 27.06 g, 267.4 mmol) under a nitrogen gas flow. After cooling the mixed solution to 10° C., a solution of acryloyl chloride (manufactured by Tokyo Chemical Industry, 23.45 g, 259.1 mmol) diluted with ethyl acetate (manufactured by Wako Pure Chemical, 50 mL) was added dropwise over 80 minutes. The mixture was then allowed to warm to room temperature and stirred for another 2 hours. After completion of stirring, the procedures according to Reference Example 1 were carried out to obtain 23.12 g of the desired product (AmEA) as a yellow liquid.

$^1$H-NMR (CDCl$_3$) δ ppm 1.90 (3H, s, HNCOCH$_3$), 3.46 (2H, m, CH$_3$CONHCH$_2$CH$_2$O), 4.16 (2H, t, CH$_3$CONHCH$_2$CH$_2$O), 5.78, 6.03, 6.34 (each 1H, dd, CH$_2$=CHCOO), 6.54 (1H, CH$_3$CONH)

Synthesis of Copolymers

Example 1

Synthesis of Copolymer (VPA/DMA=10/90)

A 200 mL three-necked flask was charged with the compound obtained in Reference Example 1 (VPA, 1.83 g, 9.99 mmol), N,N-dimethylacrylamide (DMA, manufactured by Wako Pure Chemical, 8.92 g, 90.0 mmol), 2,2'-azobis[2-(2-imidazolin-2-yl)propane] (VA-061, manufactured by Wako Pure Chemical, 25.1 mg, 0.1003 mmol) as a polymerization initiator, and tert-amyl alcohol (TAA, manufactured by Tokyo Chemical Industry, 32.25 g), and fitted with a digital thermometer, a Dimroth condenser with a three-way stopcock and a sealer with stirring blades. Next, dissolved oxygen in the mixed solution was removed by repeating 5 times the cycle of reducing the pressure to 10 mmHg and replacing with nitrogen, under ultrasonic irradiation. The reaction vessel was immersed in an oil bath and the mixture was allowed to react for 7 hours with stirring at 70° C. Then, the reaction vessel was removed from the oil bath and air-cooled to room temperature. To the polymerization reaction solution, was added 20 mL of ethanol, and the resulting mixture was stirred to lower its viscosity, followed by pouring the mixture into 500 mL of hexane to precipitate a polymer. The supernatant was removed by decantation, and the precipitated polymer was dissolved in 20 mL of ethanol. After pouring 400 mL of hexane, the supernatant was removed by decantation, and the precipitated polymer was heated and dried overnight at 40° C. in a vacuum dryer, to obtain 9.65 g (yield 90%) of a copolymer (VPA/DMA=10/90) as a white powder.

Example 2

Synthesis of Copolymer (VPA/DMA=30/70)

A 200 mL three-necked flask was charged with VPA (2.78 g, 15.2 mmol) obtained in Reference Example 1, DMA (manufactured by Wako Pure Chemical, 3.56 g, 35.9 mmol), 2,2'-azobis(2,4-dimethylvaleronitrile) (ADVN, manufactured by Wako Pure Chemical, 25.1 mg, 0.101 mmol) as a polymerization initiator, and TAA (manufactured by Tokyo Chemical Industry, 11.77 g) and fitted with a digital thermometer, a Dimroth condenser with a three-way stopcock and a sealer with stirring blades. According to the procedures in Example 1, dissolved oxygen removal, stirring under heat, reprecipitation and heat drying were carried out to obtain 4.80 g (yield 75%) of a copolymer (VPA/DMA=30/70) as a white powder.

Example 3

Synthesis of Copolymer (VPA/DMA=50/50)

A 200 mL three-necked flask was charged with VPA (4.54 g, 24.8 mmol) obtained in Reference Example 1, DMA (manufactured by Wako Pure Chemical, 2.46 g, 24.8 mmol), 2,2'-azobis[2-(2-imidazolin-2-yl)propane] (VA-061, manufactured by Wako Pure Chemical, 13.8 mg, 0.0551 mmol) as a polymerization initiator, and TAA (manufactured by Tokyo Chemical Industry, 21.13 g) and fitted with a digital thermometer, a Dimroth condenser with a three-way stopcock and a sealer with stirring blades. According to the procedures in Example 1, dissolved oxygen removal, stirring under heat, reprecipitation and heat drying were carried out to obtain 4.80 g (yield 68%) of a copolymer (VPA/DMA=50/50) as a white powder.

Number average molecular weight (Mn)=59510; Mass average molecular weight (Mw)=224020.

Example 4

Synthesis of Copolymer (AcEA/DMA=10/90)

A 200 mL four-necked flask was charged with TAA (manufactured by Tokyo Chemical Industry, 20.15 g), and fitted with a dropping funnel, a digital thermometer, a Dimroth condenser with a three-way stopcock and a sealer with stirring blades. Next, dissolved oxygen in the solvent was removed by bubbling with nitrogen for 10 minutes. The reaction vessel was immersed in an oil bath and the mixture was stirred at 95° C.

A mixed solution of the compound obtained in Reference Example 2 (AcEA, 1.76 g, 11.4 mmol), DMA (manufactured by Wako Pure Chemical, 8.92 g, 90.0 mmol), 2,2'-azobis (isobutyronitrile) (AIBN, manufactured by Wako Pure Chemical, 65.5 mg, 0.399 mmol) as a polymerization initiator, and TAA (manufactured by Tokyo Chemical Industry, 10.0 g) was placed in a dropping funnel and dropped into a reaction vessel over 2.5 hours, and then allowed to react at 95° C. with stirring for 30 minutes. Then, the reaction vessel was removed from the oil bath and air-cooled to room temperature. To the polymerization reaction solution, was added 60 mL of ethanol and the resulting mixture was stirred to lower its viscosity, followed by pouring the mixture into 800 mL of hexane to precipitate a polymer. The supernatant was removed by decantation, and the precipitated polymer was dissolved in 50 mL of ethanol. After pouring acetone (100 mL)/hexane (600 mL) mixed solution, the supernatant was removed by decantation, and the precipitated polymer was heated and dried overnight at 40° C. in a vacuum dryer, to obtain 9.20 g (yield 86%) of a copolymer (AcEA/DMA=10/90) as a white powder.

Example 5

Synthesis of Copolymer (AmEA/DMA=10/90)

A 200 mL four-necked flask was charged with TAA (manufactured by Tokyo Chemical Industry, 20.15 g), and fitted with a dropping funnel, a digital thermometer, a Dimroth condenser with a three-way stopcock and a sealer with stirring blades. Next, dissolved oxygen in the solvent was removed by bubbling with nitrogen for 10 minutes. The reaction vessel was immersed in an oil bath and stirred at 95° C.

A mixed solution of the compound obtained in Reference Example 3 (AmEA, 1.57 g, 8.57 mmol), DMA (manufactured by Wako Pure Chemical, 8.92 g, 90.0 mmol), AIBN (manufactured by Wako Pure Chemical, 65.5 mg, 0.399 mmol) as a polymerization initiator, TAA (manufactured by Tokyo Chemical Industry, 10.0 g) was placed in a dropping funnel and dropped into a reaction vessel over 2.5 hours, and then allowed to react at 95° C. with stirring for 3.5 hours. Then, the reaction vessel was removed from the oil bath and air-cooled to room temperature. To the polymerization reaction solution, was added 60 mL of ethanol and the resulting mixture was stirred to lower its viscosity, followed by pouring the mixture into 600 mL of hexane to precipitate a polymer. The supernatant was removed by decantation, and the precipitated polymer was dissolved in 60 mL of ethanol. After pouring acetone (50 mL)/hexane (550 mL), the supernatant was removed by decantation, and the precipitated polymer was heated and dried overnight at 40° C. in a vacuum dryer, to obtain 8.86 g (yield 84%) of a copolymer (AmEA/DMA=10/90) as a white powder.

Comparative Example 1

Synthesis of PolyVPA (PVPA)

A 200 mL three-necked flask was charged with VPA (4.58 g, 25.0 mmol) obtained in Reference Example 1, VA-061 (manufactured by Wako Pure Chemical, 6.3 mg, 0.0252 mmol) as a polymerization initiator, TAA (manufactured by Tokyo Chemical Industry, 10.68 g) and fitted with a digital thermometer, a Dimroth condenser with a three-way stopcock and a sealer with stirring blades. Next, dissolved oxygen in the mixed solution was removed by repeating 5 times the cycle of reducing the pressure to 10 mmHg and replacing with nitrogen, under ultrasonic irradiation. The reaction vessel was immersed in an oil bath and the mixture was allowed to react for 7 hours with stirring at 70° C. Then, the reaction vessel was removed from the oil bath and air-cooled to room temperature. To the polymerization reaction solution, was added 20 mL of ethanol and the resulting mixture was stirred to lower its viscosity, followed by pouring the mixture into 500 mL of hexane to precipitate a polymer. The supernatant was removed by decantation, and the precipitated polymer was dissolved in 20 mL of ethanol. After pouring 400 mL of hexane, the supernatant was removed by decantation, and the precipitated polymer was heated and dried overnight at 40° C. in a vacuum dryer, to obtain 3.51 g of a polymer (PVPA) as a yellow sticky solid.

Comparative Example 2

Synthesis of PDMA

A polymer (PDMA) was obtained by carrying out the same polymerization reaction as in Reference Example 4 except that VPA was replaced with DMA (manufactured by Wako Pure Chemical).

Mass average molecular weights (Mw), number average molecular weights (Mn) and Mw/Mn of the polymers obtained in Examples 1 to 5 and Comparative Examples 1 to 2 are shown in Table 1.

TABLE 1

| Example No. | Polymer Type | Mw (kD) | Mn (kD) | Mw/Mn |
|---|---|---|---|---|
| Example 1 | VPA/DMA = 10/90 | 326 | 95.5 | 3.4 |
| Example 2 | VPA/DMA = 30/70 | 411 | 113 | 3.6 |
| Example 3 | VPA/DMA = 50/50 | 224 | 59.5 | 3.8 |
| Example 4 | AcEA/DMA = 10/90 | 218 | 42.3 | 5.2 |
| Example 5 | AmEA/DMA = 10/90 | 87.5 | 20.9 | 4.2 |
| Comparative Example 1 | PVPA | 103 | 16.9 | 6.1 |
| Comparative Example 2 | PDMA | 369 | 135 | 2.7 |

Evaluation of Lubricity and Scrubbing Durability

Example 6

Five milliliters of a borate buffer solution (pH 7.1 to 7.3) containing 750 ppm of the copolymer obtained in Example 1 was added to a glass vial bottle. A commercially available contact lens "2 Week ACUVUE" (registered trademark) (manufactured by Johnson & Johnson) was immersed in the solution, steam sterilized (121° C., 30 minutes), and evaluated for lubricity and scrubbing durability by the above analysis method and evaluation method (2).

Examples 7 to 10

Lubricity and so on were evaluated in the same manner as in Example 6 except that the copolymer obtained in Example 1 was changed to the copolymer obtained in Examples 2 to 5, respectively, as shown in Table 2.

Comparative Examples 3 to 4

Lubricity and scrubbing durability were evaluated in the same manner as in Example 6 except that the copolymer obtained in Example 1 was changed to the copolymer obtained in Comparative Examples 1 to 2, respectively, as shown in Table 2.

Comparative Example 5

Lubricity and scrubbing durability were evaluated in the same manner as in Example 6 except that the copolymer obtained in Example 1 was changed to polyvinylpyrrolidone (PVP) (commercially available: PVP-K90) as shown in Table 2.

Comparative Example 6

Lubricity and so on were evaluated in the same manner as in Example 6 except that the copolymer obtained in Example 1 was changed as shown in Table 2.

The evaluation results of the initial lubricity in Examples 6 to 10 and Comparative Examples 3 to 6 are shown in Table 2. The evaluation results of scrubbing durability in Examples 6 to 10 and Comparative Examples 3 to 5 are shown in FIG. 1.

TABLE 2

| | Polymer Type | Polymer Concentration in Solution (ppm) | Initial Lubricity [1 (Bad) to 5 (Excellent)] |
|---|---|---|---|
| Example 6 | VPA/DMA = 10/90 | 750 | 5 |
| Example 7 | VPA/DMA = 30/70 | 750 | 5 |
| Example 8 | VPA/DMA = 50/50 | 750 | 4.5 |
| Example 9 | AcEA/DMA= 10/90 | 750 | 5 |
| Example 10 | AmEA/DMA = 10/90 | 750 | 5 |
| Comparative Example 3 | PVPA | 750 | 3.5 |
| Comparative Example 4 | PDMA | 750 | 5 |
| Comparative Example 5 | PVP | 750 | 4.5 |
| Comparative Example 6 | none | 0 | 2 |

Coefficient of Dynamic Friction and DCA Hysteresis

Examples 11 to 13

The coefficient of dynamic friction and the DCA hysteresis were measured by the above analysis method and evaluation methods (3) and (4) using the contact lenses whose surfaces were coated in Examples 6 to 8, respectively.

Comparative Example 7

Using a commercially available contact lens "1-Day ACUVUE" (registered trademark) and "Moist" (registered trademark) (manufactured by Johnson & Johnson) for comparison, the coefficient of dynamic friction and the DCA hysteresis were measured in the same manner as in Example 11. The measurement results of the coefficient of dynamic friction (MIU), dynamic contact angle (DCA), and DCA hysteresis in Examples 11 to 13 and Comparative Example 7 are shown in Table 3.

TABLE 3

| | Coefficient of Dynamic Friction (MIU) | DCA Forward (°) | DCA Backward (°) | DCA hysteresis |
|---|---|---|---|---|
| Example 11 | 0.191 | 44.84 | 50.65 | 5.81 |
| Example 12 | 0.202 | 47.19 | 51.92 | 4.73 |
| Example 13 | 0.105 | 32.29 | 29.20 | 4.55 |
| Comparative Example 7 | 0.268 | 50.90 | 40.99 | 9.91 |

Solubility of Copolymer in Aqueous Solution

Example 14

Ten milligrams of the copolymer obtained in Example 2 and 0.090 mL of a borate buffer solution (pH 7.1 to 7.3) were added to a glass vial bottle and shaken. The obtained solution was colorless and transparent, indicating that the copolymer obtained in Example 2 was completely dissolved.

Example 15

Ten milligram of the copolymer obtained in Example 4 and 0.090 mL of a borate buffer solution (pH 7.1 to 7.3) were added to a glass vial bottle and shaken. The obtained solution was colorless and transparent, indicating that the copolymer obtained in Example 4 was completely dissolved.

Comparative Example 8

The polymer (PVPA) obtained in Comparative Example 1 in an amount of 1.0 mg and 0.90 mL of a borate buffer solution (pH 7.1 to 7.3) were added to a glass vial bottle and shaken. Insoluble matter was observed in the obtained solution, indicating that PVPA was not completely dissolved.

Wearing Model Test

Example 16

An eyeball model was prepared by pouring an aqueous 60% by mass acrylamide solution into a hemispherical metal mold, adding ammonium persulfate to 1% by mass, and leaving the resultant at 60° C. for 6 hours.

Figure 2:
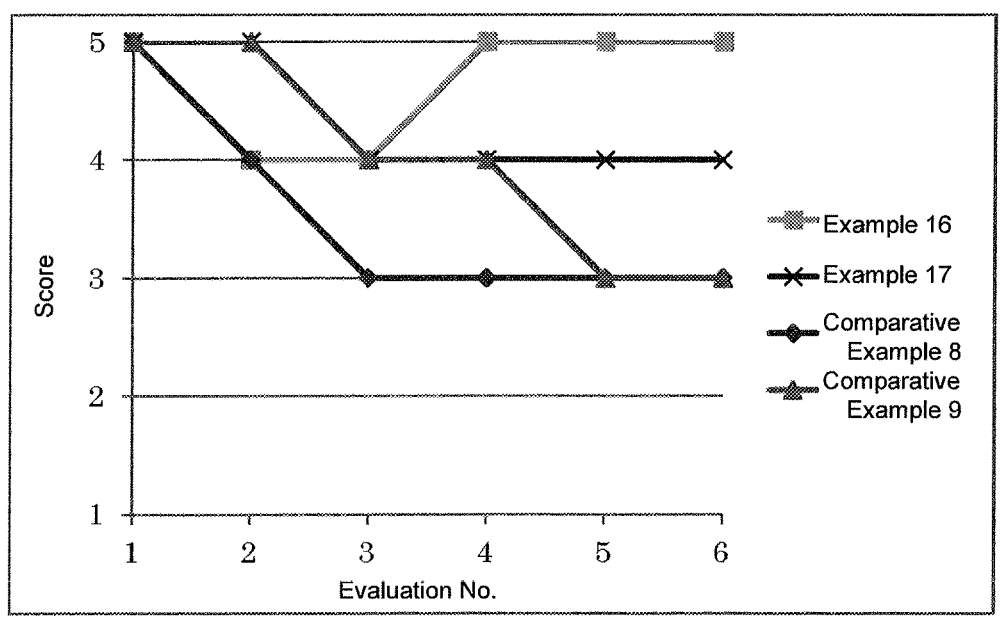
FIG. 2 shows the test results of wearing model test for the surface-coated contact lenses produced in Examples 16 and 17 and Comparative Examples 8 and 9.

A contact lens prepared in the same manner as in Example 6 except that a borate buffer solution containing 200 ppm of the copolymer obtained in Example 2 was used was placed on the eyeball model prepared above. Vertical and horizontal movement of the lens on the model; wetted appearance by visual observation; degree of adherence in removing the lens from the model when wetted appearance by visual observation disappears were scored based on the following five-point scale. The score results obtained by a total of six evaluations using the same contact lens are shown in FIG. 2.

5: Moves very well on the model, maintains the wet state for a long time, and shows little resistance when being removed.

4: Moves well on the model, maintains the wet state for a certain period of time, and shows low resistance when being removed.

3: Moves on the model, maintains the wet state for a short time, and shows some resistance when being removed.

2: Moves little on the model, maintains the wet state for a very short time, and shows a considerable resistance when being removed.

1: Does not move on the model, does not maintain the wet state, and is difficult to remove.

Example 17

A contact lens was prepared in the same manner as in Example 6 except that a borate buffer solution containing 200 ppm of the copolymer obtained in Example 4 was used, and evaluated in the same manner as in Example 16.

Comparative Example 9

A contact lens was prepared in the same manner as in Example 6 except that a borate buffer solution containing 500 ppm of the polymer obtained in Comparative Example 2 was used, and evaluated in the same manner as in Example 16.

Comparative Example 10

A contact lens was prepared in the same manner as in Example 6 except that a borate buffer solution containing 500 ppm of polyvinylpyrrolidone (PVP) (commercially available: PVP-K90) was used, and evaluated in the same manner as in Example 16.

INDUSTRIAL APPLICABILITY

The solution containing the copolymer according to the present invention can be used for improving the lubricity and scrubbing durability of medical devices such as ophthalmic lenses (e.g., intraocular lenses, contact lenses, and spectacle lenses), endoscopes, catheters, and infusion tubes.

The invention claimed is:

1. A medical device comprising a substrate, and a copolymer on at least a part of the surface of said substrate,
    wherein the copolymer is water-soluble and comprises as constitutional units the following monomers A and B:
    monomer A: a monomer containing a (meth)acryloyl group and an ester or amide structure in a molecule, wherein said ester or amide structure is not constituted by including a part of said (meth)acryloyl group; and
    monomer B: a monomer containing a (meth)acrylamide group in a molecule and having a structure different from that of said monomer A;
    wherein said monomer A is a compound represented by the following formula [I]:

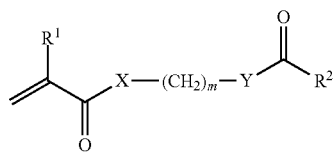

wherein,
  $R^1$ represents hydrogen or ethyl;
  $R^2$ represents alkyl;
  X represents oxygen or $NR^3$, wherein $R^3$ represents hydrogen or alkyl;
  Y represents $NR^4$, wherein $R^4$ represents hydrogen or alkyl;
  $R^4$ and $R^2$ optionally together form a ring structure; and
  m represents an integer from 1 to 4.

2. The medical device according to claim 1, wherein said monomer B is a compound represented by the following formula [III]:

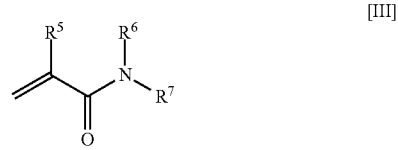

wherein,
  $R^5$ represents hydrogen or methyl; and
  $R^6$ and $R^7$ each independently represent hydrogen or alkyl; or $R^6$ and $R^7$ optionally together form a ring structure.

3. The medical device according to claim 1, wherein the monomer A content is 5 to 50 mol %, and the monomer B content is 50 to 95 mol %.

4. The medical device according to 1, which is an ophthalmic lens.

5. The medical device according to claim 4, wherein sail ophthalmic lens is a contact lens.

6. A medical device comprising a substrate, and a copolymer on at least a part of the surface of said substrate,
    wherein the copolymer is water-soluble and comprises as constitutional units the following monomers A and B:
    monomer A: a monomer containing a (meth)acryloyl group and an ester or amide structure in a molecule, wherein said ester or amide structure is not constituted by including a part of said (meth)acryloyl group; and
    monomer B: a monomer containing a (meth)acrylamide group in a molecule and having a structure different from that of said monomer A:
    wherein said monomer A is a compound represented by the following formula [II]:

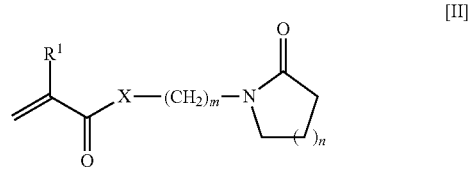

wherein,
  $R^1$ represents hydrogen or methyl;
  X represents oxygen or $NR^3$, wherein $R^3$ represents hydrogen or alkyl;
  m represents an integer from 1 to 4; and
  n represents an integer from 1 to 3.

7. The medical device according to claim 6, which is an ophthalmic lens.

8. The medical device according to claim 7, wherein said ophthalmic lens is a contact lens.

9. The medical device according to claim 6, wherein said monomer B is a compound represented by the following formula [III]:

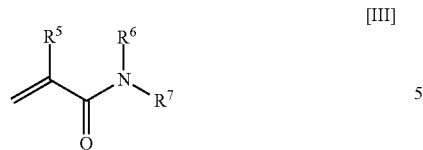
[III]
wherein,
R⁵ represents hydrogen or methyl; and
R⁶ and R⁷ each independently represent hydrogen or alkyl; or R⁶ and R⁷ optionally together form a ring structure.
10. The medical device according to claim 6, wherein the monomer A content is 5 to 50 mol %, and the monomer B content is 50 to 95 mol %.
* * * * *

UNITED STATES PATENT AND TRADEMARK OFFICE
CERTIFICATE OF CORRECTION

PATENT NO. : 11,591,426 B2
APPLICATION NO. : 17/035860
DATED : February 28, 2023
INVENTOR(S) : Kyohei Yamashita It is certified that error appears in the above-identified patent and that said Letters Patent is hereby corrected as shown below:

In the Claims

In Claim 1, Column 21, Line 60, "R1 represents hydrogen or ethyl;" should read -- R1 represents hydrogen or methyl; --

In Claim 5, Column 22, Line 26, "wherein sail" should read -- wherein said --

Signed and Sealed this
Ninth Day of May, 2023

Katherine Kelly Vidal
*Director of the United States Patent and Trademark Office*